United States Patent
Cushion et al.

(10) Patent No.: US 9,901,654 B2
(45) Date of Patent: Feb. 27, 2018

(54) MODULAR MEDICAL INSTRUMENT STERILIZATION CONTAINER AND RELATED METHODS

(71) Applicant: Symmetry Medical Manufacturing, Inc., Warsaw, IN (US)

(72) Inventors: Robert Cushion, Manchester, NH (US); George P. Hannafin, Hudson, NH (US)

(73) Assignee: Symmetry Medical Manufacturing, Inc., Warsaw, IN (US)

(*) Notice: Subject to any disclaimer, the term of this patent is extended or adjusted under 35 U.S.C. 154(b) by 745 days.

(21) Appl. No.: 14/098,899

(22) Filed: Dec. 6, 2013

(65) Prior Publication Data
US 2014/0158570 A1   Jun. 12, 2014

Related U.S. Application Data

(60) Provisional application No. 61/734,055, filed on Dec. 6, 2012.

(51) Int. Cl.
*A61L 2/26* (2006.01)

(52) U.S. Cl.
CPC .......... *A61L 2/26* (2013.01); *A61L 2202/182* (2013.01); *Y10T 29/49947* (2015.01)

(58) Field of Classification Search
CPC ............................. A61L 2/26; Y10T 29/49947
USPC ...... 206/438; 220/4.33, 4.34, 617, 621, 622, 220/610, 4.28, 676
See application file for complete search history.

(56) References Cited

U.S. PATENT DOCUMENTS

| | | | |
|---|---|---|---|
| 2,869,750 A * | 1/1959 | Doerr et al. ................. | 220/4.28 |
| 2,919,826 A * | 1/1960 | Richter ......................... | 220/1.5 |
| 3,315,639 A | 4/1967 | Close | |
| 3,374,915 A * | 3/1968 | Verhein et al. .............. | 220/4.28 |
| 3,517,849 A * | 6/1970 | Presnick ...................... | 220/4.28 |
| 3,572,535 A * | 3/1971 | Kinzie ......................... | 220/4.33 |
| 3,784,043 A * | 1/1974 | Presnick ...................... | 220/4.28 |
| 5,037,027 A * | 8/1991 | Nichols ...................... | 229/198.1 |
| 5,424,049 A | 6/1995 | Riley | |
| 5,452,830 A * | 9/1995 | Hopkins et al. .............. | 224/666 |
| 5,690,275 A * | 11/1997 | Bose et al. ................... | 229/120 |
| 5,720,403 A * | 2/1998 | Sawyer ........................ | 217/65 |
| 5,732,821 A | 3/1998 | Stone et al. | |
| 5,913,422 A | 6/1999 | Cote et al. | |
| 6,138,850 A | 10/2000 | Berry, III | |
| 6,460,724 B1 * | 10/2002 | Bradford ....................... | 220/642 |
| 6,808,074 B1 * | 10/2004 | Schwartz ...................... | 206/577 |
| 6,832,580 B2 * | 12/2004 | Marchioro .................... | 119/452 |

(Continued)

*Primary Examiner* — Steven A. Reynolds
(74) *Attorney, Agent, or Firm* — Hayes Soloway PC (57) ABSTRACT

A modular medical instrument sterilization container and related methods are disclosed. The container includes a base and a plurality of sidewalls, each being substantially planar and having a consistently repeated cross-section. A plurality of corner posts having a uniform, consistent cross-section is connected between the plurality of sidewalls. A plurality of bottom edge rails having a uniform, consistent cross-section is connected between a sidewall and the base. A plurality of top edge rails having a uniform, consistent cross-section is connected to the sidewall. A plurality of junction connectors are connected between one of the plurality of corner posts and at least one of: two of the bottom edge rails and two of the top edge rails.

2 Claims, 7 Drawing Sheets

(56) References Cited

U.S. PATENT DOCUMENTS

| | | |
|---|---|---|
| 6,874,634 B2 | 4/2005 | Riley |
| 6,896,149 B1 * | 5/2005 | Berry, III .................... 220/4.28 |
| 7,267,229 B2 * | 9/2007 | Chen ............................ 206/600 |
| 7,341,148 B2 | 3/2008 | Bettenhausen et al. |
| 7,909,191 B2 | 3/2011 | Baker et al. |
| 8,177,776 B2 | 5/2012 | Humayun et al. |
| 8,241,587 B2 | 8/2012 | Friderich et al. |
| 2002/0071799 A1 | 6/2002 | Wood |
| 2006/0191943 A1 | 8/2006 | Dane et al. |
| 2006/0273084 A1 | 12/2006 | Baker et al. |
| 2007/0144926 A1 | 6/2007 | Bettenhausen et al. |
| 2009/0071957 A1 * | 3/2009 | Chang ......................... 220/4.33 |
| 2010/0158753 A1 | 6/2010 | Friderich et al. |
| 2010/0252468 A1 | 10/2010 | Pratte et al. |
| 2011/0011855 A1 * | 1/2011 | Han ............................ 220/4.33 |
| 2011/0108554 A1 | 5/2011 | Ladison et al. |
| 2011/0114522 A1 | 5/2011 | Alston et al. |
| 2012/0082589 A1 | 4/2012 | Ladison et al. |
| 2012/0180439 A1 | 7/2012 | Klenk |

\* cited by examiner

MODULAR MEDICAL INSTRUMENT STERILIZATION CONTAINER AND RELATED METHODS

CROSS REFERENCE TO RELATED APPLICATION

This application claims benefit of U.S. Provisional Application Ser. No. 61/734,055 entitled, "Modular Medical Instrument Sterilization Container and Related Methods" filed Dec. 6, 2012, the entire disclosure of which is incorporated herein by reference.

FIELD OF THE DISCLOSURE

The present disclosure is generally related to containers and more particularly is related to a modular medical instrument sterilization container and related methods.

BACKGROUND OF THE DISCLOSURE

Sterilization containers or cases are known that provide organization, storage and sterilization functionality for surgical instruments and devices. In order to avoid infection to a patient on which such instruments are used, the instruments are required to be cleaned and sterilized after a procedure, and therefore, before use. The medical instruments, when contaminated, are run through an autoclave while held within a sterilization case.

Surgical procedures are regularly performed using sets of pre-selected surgical instruments, each set being a collection of instruments established from experience or design to be useful in a given surgical procedure. The surgical instruments expected to be used in a particular procedure are grouped together to form a set, and, as a set, are sterilized, stored on a pan or tray, and finally transported on that pan or tray to the operating room when their use is required. Complex procedures typically involve a substantial number of instruments. Thus, typically, several instrument trays may be necessary to accommodate all of the required surgical instruments. Accordingly, sterilizing cases often are designed to accommodate a plurality of trays with the instruments arranged on the trays in such a manner that the trays may be accessed as the surgical procedure advances often in a preset sequence.

Sterilization cases are generally purchased remotely from a manufacturer and shipped to the customer. Cases are generally shipped inefficiently, since they require large boxes and packing materials to ensure that the cases are not damaged during transport. If a sterilization case were to be damaged, it may be cracked or deformed causing small crevices and areas that are prone to harboring bacteria. These areas can complicate proper sterilization of the case and the instruments therein. Additionally, many containers, including sterilization cases, are shipped assembled and occupy significantly more space during shipping than would be required if the containers could be shipped unassembled, thereby increasing shipping costs.

Thus, a heretofore unaddressed need exists in the industry to address the aforementioned deficiencies and inadequacies.

SUMMARY OF THE DISCLOSURE

Embodiments of the present disclosure provide a system and method for a modular medical instrument sterilization container. Briefly described, in architecture, one embodiment of the system, among others, can be implemented as follows. The modular medical instrument sterilization has a base and a plurality of sidewalls, wherein the base and the plurality of sidewalls are both substantially planar and have a consistently repeated cross-section. A plurality of corner posts are connected between at least two of the plurality of sidewalls, wherein all of the plurality of corner posts have a uniform, consistent cross-section along a length. A plurality of bottom edge rails are connected between at least one of the plurality of sidewalls and the base, wherein the bottom edge rail is connected to a first edge of the at least one sidewall, wherein all of the plurality of bottom edge rails have a uniform, consistent cross-section along a length. A plurality of top edge rails connected to a second edge of the at least one sidewall, wherein the second edge is opposite the first edge, wherein all of the plurality of top edge rails have a uniform, consistent cross-section along a length. A plurality of junction connectors are connected between one of the plurality of corner posts and at least one of: two of the plurality of bottom edge rails and two of the plurality of top edge rails.

The present disclosure can also be viewed as providing methods for constructing a modular medical sterilization container. In this regard, one embodiment of such a method, among others, can be broadly summarized by the following steps: cutting a quantity of substantially planar material having a consistently repeated cross-section to form a base and a plurality of sidewalls; cutting at least one corner post structure having a uniform, consistent cross-section, whereby at least a portion of the cut corner post structure forms a plurality of corner posts; cutting at least one bottom edge rail structure having a uniform, consistent cross-section, whereby at least a portion of the bottom edge rail structure forms a plurality of bottom edge rails; cutting at least one top edge rail structure having a uniform, consistent cross-section, whereby at least a portion of the cut top edge rail structure forms a plurality of top edge rails; connecting together each of the plurality of corner post between at least two of the plurality of sidewalls; connecting together each of the plurality of bottom edge rails between at least one sidewall of the plurality of sidewalls and the base, wherein the bottom edge rail is connected to a first edge of the sidewall; connecting together each of the plurality of top edge rails to a second edge of the sidewall, wherein the second edge is opposite the first edge; and using a plurality of junction connectors, connecting each of the corner posts with at least one of: two bottom edge rails; and two top edge rails.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
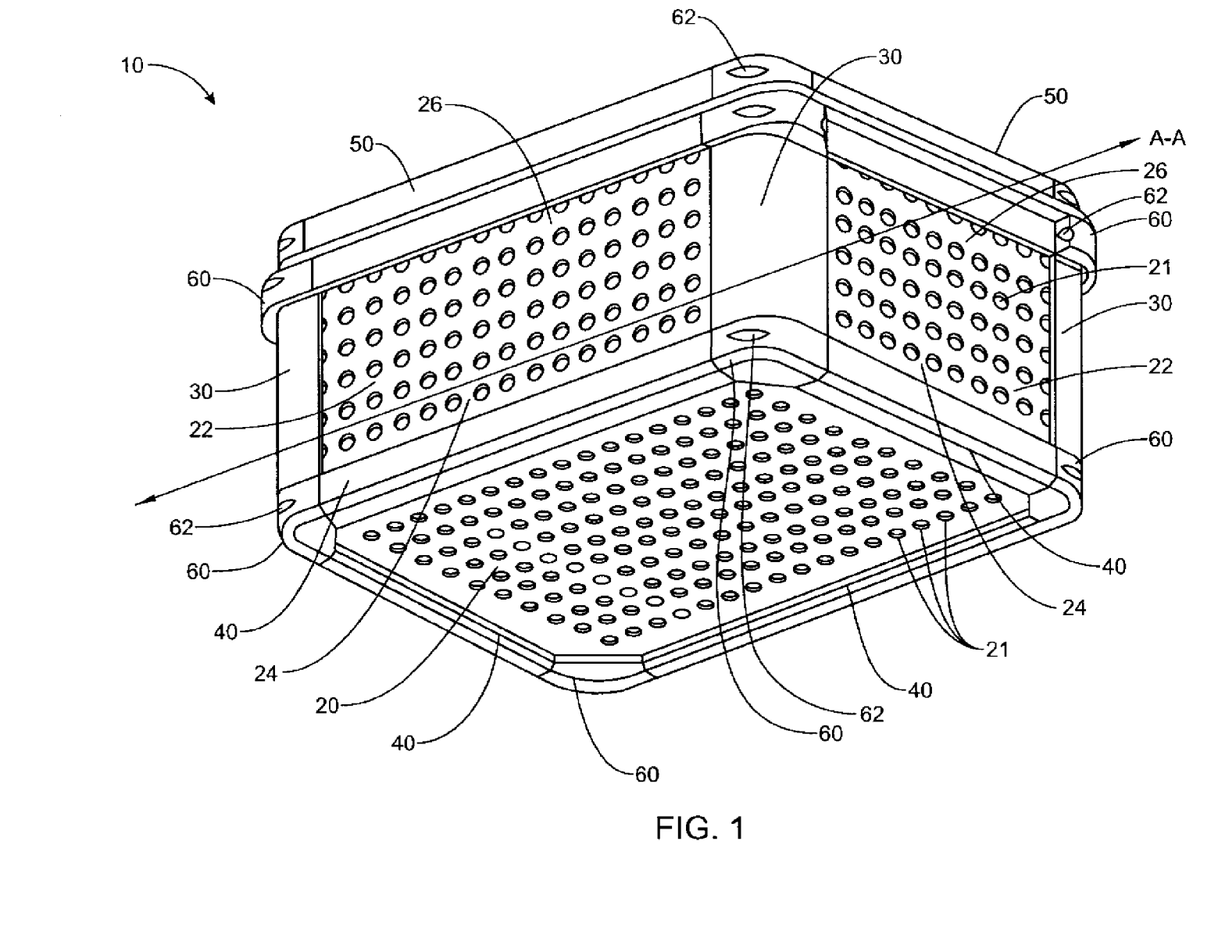
FIG. 1 is a plan view illustration of a modular medical instrument sterilization container, in accordance with a first exemplary embodiment of the present disclosure.

FIG. 1 is a plan view illustration of a modular medical instrument sterilization container 10, in accordance with a first exemplary embodiment of the present disclosure. The modular medical instrument sterilization container 10, which may be referred to herein simply as 'container 10' includes a base 20 and a plurality of sidewalls 22 which are both substantially planar and have consistently repeated cross-sections. Each of a plurality of corner posts 30 is connected between at least two of the plurality of sidewalls 22, wherein all of the plurality of corner posts 30 have a uniform, consistent cross-section along a length. Each of a plurality of bottom edge rails 40 is connected between at least one of the plurality of sidewalls 22 and the base 20, wherein the bottom edge rail 40 is connected to a first edge 24 of the at least one sidewall 22, wherein all of the bottom edge rails 40 have a uniform, consistent cross-section along a length. Each of a plurality of top edge rails 50 is connected to a second edge 26 of the at least one sidewall 22, wherein the second edge 26 is opposite the first edge 24, wherein all of the plurality of top edge rails 50 have a uniform, consistent cross-section along a length. Each of a plurality of junction connectors 60 is connected between a corner post 30 and at least one of: two of the plurality of bottom edge rails 40 and two of the plurality of top edge rails 50.

The container 10 may be used to store and house medical instruments throughout a variety of medical processes and operations, including during sterilization processes, during pre and post operation procedures, and in storage. The container 10 may have substantial benefits when used as a vessel for housing the medical instruments during a sterilization process, such as a sterilization process involving high temperatures, moisture, chemicals, or other sterilants.

The container 10 is modular and can be formed to any size that is desired by the user, and with any materials required by the intended use of the container 10. The materials used may utilize varying colors for quick identification of the container 10. In accordance with this disclosure, the modularity of the container 10 may be characterized as the container 10 being formed from a plurality of components that can be sized to different dimensions, wherein the container 10 can be assembled into a substantially unitary structure from the components. As is described herein, the various components that form the container 10 may be beneficial due, at least in part, to their abilities to provide many options for sizing of the container 10.

As is shown in FIG. 1, the base 20 and a plurality of sidewalls 22 are both formed from at least one substantially planar material that has a consistently repeated cross-section. For example, the base 20 and the plurality of sidewalls 22 may be formed from a planar sheet of aluminum that has a length and height dimension that substantially exceeds a thickness dimension. The base 20 and the plurality of sidewalls 22 may be formed from the same material and preferably formed from the same quantity or sheet of material. For instance, a single sheet of aluminum may be cut to form the base 20 and the sidewalls 22. The base 20 and sidewalls 22 may have various holes 21, or similar structures, such as slots, gaps, or perforations, for allowing sterilant to travel through the container 10. Any type of material may be used to make the base 20 and sidewalls 22.

Both the base 20 and the sidewalls 22 have a consistently repeated cross-section, in that, the cross-section of any given location or portion of the base 20 and the sidewalls 22 will substantially match the cross-section of any other location or portion of the base 20 and sidewalls 22. For example, the base 20 and the sidewalls 22 may have a repeating pattern of holes 21, slots, or other features which yield a consistently repeated cross-section. Since the base 20 and sidewalls 22 may have holes 21, one having skill in the art can see that the cross-section of a position on the base 20 that corresponds to the location of a hole 21 may have a different cross-section than a location without a hole 21. Accordingly, the consistently repeated cross-section of the base 20 and sidewalls 22 may allow for the inclusion of a pattern of repeatable features, such as the holes 21. Other consistently repeated cross-sections may include a base 20 and sidewalls 22 that have a fully planar without holes 21, have any type of textured surface(s), have repeatable varying thicknesses, or other features that form a consistent pattern throughout the base 20 and the sidewalls 22.

The sidewalls 22 may be connected together with the corner posts 30, wherein a single corner post 30 is connected between two of the sidewalls 22. The connection between the sidewalls 22 and the corner posts 30 may include any of a variety of different connections, such as a friction-fit connection, an adhesive connection, a male/female connection, or any other types, such that the connection doesn't prevent the sidewalls 22 from having a consistently repeated cross-section. For example, the corner posts 30 may have a slot formed along an entire length thereof that receives the edge of the sidewalls 22. It is noted that the engagement between the sidewalls 22 and the corner posts 30 may be such that the structures are retained together without the aid of other structures or components, or such that the structures are positioned engaged with each other but retained by the use of other structures or components. For example, the sidewalls 22 may be fixedly engaged with the corner posts 30 (such that the sidewalls 22 are fully stationary relative to the corner posts 30), or non-fixedly engaged with the corner posts 30 (such that the sidewalls 22 are slightly movable within the slots) but held in an engaged position with the junction connectors 60. Any number of sidewalls 22 may be used with any number of corner posts 30 to form a container 10 with any shape, dimension, or size, all of which are considered within the scope of the present disclosure.

In a similar fashion to that of the corner post 30, the bottom edge rail 40 is connected between at least two sidewalls 22 and the base 20. The bottom edge rail 40 may generally be positioned substantially perpendicular to the corner post 30, as is shown in FIG. 1, however orientations of other angles are possible. In the same manner as with the corner post 30, the engagement between the bottom edge rail 40 and the sidewalls 22 and base 20 may be a fixed or non-fixed connection. The top edge rail 50 is connected to a second edge 26 of the sidewall 22 and may be positioned substantially perpendicular to the corner post 30. The bottom edge rail 40 and the top edge rail 50 are connected to opposing sides of the sidewalls 22. For example, the bottom edge rail 40 is connected to the first edge 24 of the sidewall 22, whereas the top edge rail 50 is connected to the second edge 26 of the sidewall 22. The other edges of the sidewall 22, which may be referred to herein as a third edge, may be connected to a corner post 30. It may be preferred for all edges of the base 20 and all sidewalls 22 to be connected to the bottom edge rail 40, the top edge rail 50, or a corner post 30. It is noted that the bottom and top edge rails 40, 50 may have the same uniform, consistent cross-section, thereby allowing them to be interchangeable with one another.

A plurality of junction connectors 60 are connected between a corner post 30 and two of the bottom edge rails 40 or between a corner post 30 and two of the top edge rails 50. The junction connectors 60 may retain the bottom and top edge rails 40, 50 to the corner posts 30, thereby holding the container 10 in a shape predetermined by the dimensions of the various components. The junction connectors 60 may utilize any type of fastener connection (generally denoted by reference character 62), such as threaded fasteners, friction fasteners, biased fasteners, or a combination thereof. For example, the junction connectors 60 may use a friction fastener engagement with the corner posts 30 and a threaded fastener engagement with the bottom and top side rails 40, 50, described more relative FIG. 3. The junction connectors 60 may provide for permanent or removable connections between the components of the container 10.

An important aspect of the container 10 is that many of the components have a uniform, consistent cross-section along their entire length. For example, all of the corner posts 30 have a uniform, consistent cross-section along a length, all of the bottom edge rails 40 have a uniform, consistent cross-section along their length, and all of the top edge rails 50 have a uniform, consistent cross-section along a length. The consistent cross-section along the length of the various components means that the cross-section at any given position along the length of the component will be the same as the cross-section at another position along the length. Thus, from one end to an opposing end, the cross-section of each of the components will be fully uniform, allowing for each of the components to be formed from extrusion through a two-dimensional (2D) die. It is noted that the cross-section of one component, such as the corner post 30, may be different from the cross-section of a different component, such as the top edge rail 50.

In the first exemplary embodiment shown in FIG. 1, the container 10 includes one base 20, four sidewalls 22, four corner posts 30, four bottom edge rails 40, four top edge rails 50, and a plurality of junction connectors 60 positioned between the corner posts 30 and either the bottom or top edge rails 40, 50, as the case may be. The container 10 may optionally include a cover 70 that may be formed from the same materials and design as the rest of the container 10. For example, the modular cover section 70 may be formed with a planar sheet of center material (FIG. 4) that is abutted on the edges with rails held together with junction connectors 60. The container 10 may be manufactured to allow for nesting of many containers 10, such as having the base 20 or bottom edge rails 40 of one container 10 nest or engage with the top edge rails 50 or cover 70 of another container.

One of the benefits of the container 10 is its modularity and ease of manufacture. The container 10 can be built to variety of sizes utilizing the same stock of materials, thus allowing the container to easily be built to any specification without manufacturing various sized molds, without retooling of machines, utilizing timely manufacturing operations, like bending, and without other manufacturing constraints and costs. Conventional containers are commonly formed from molding sheets of material into a three-dimensional (3D) part, such as a base that has walls integrally formed from the same material. When a new size container is needed, the manufacturer must retool the machinery, which is expensive and time consuming. The design disclosed herein allows for manufacture, for example, of 8-foot edge rails 40, 50 and 8-foot corner posts 30 and sheets of base 20 and sidewall 22 that are 4-foot by 8-foot, which can be cut to custom-requested size and assembled and may be more cost-effective and less labor intensive than manufacturing, for example, 4-inch corner posts, 5-inch corner posts, 6-inch corner posts, etc. along with a range of edge rails 40, 50 sizes and a range of side wall sizes and a range of bottom sizes and sorting and inventorying each size for eventual assembly.

However, the container 10 may be manufactured by simply cutting the base 20 and the sidewalls 22, and cutting the lengths of the corner posts 30, the bottom edge rails 40, and the top edge rails 50. The uniform, consistent cross-section of each of these components allows single length of each of the components, e.g., 48", to be cut into four lengths of approx. 12" without further processing. Once the components are cut to the proper sizes and lengths, they may be retained together with the junction connectors 60. By providing the base 20 and the sidewalls 22 with a consistently repeated cross-section, and the corner posts 30, bottom and top edge rails 40, 50 with a uniform, consistent cross-section, the manufacture can produce an infinite number of differently-sized containers 10 by simply varying the length and width dimensions of the base 20 and sidewalls 22, and the length of the corner posts 30, and bottom and top edge rails 40, 50. The manufacturer may be capable of building the container 10 utilizing a small inventory of parts and components, and ultimately produce the container 10 quicker than conventional containers, deliver the container 10 with the option of customer-assembly, or allow for the customer to reconfigure the components to form different sizes of the container 10.

Figure 2:
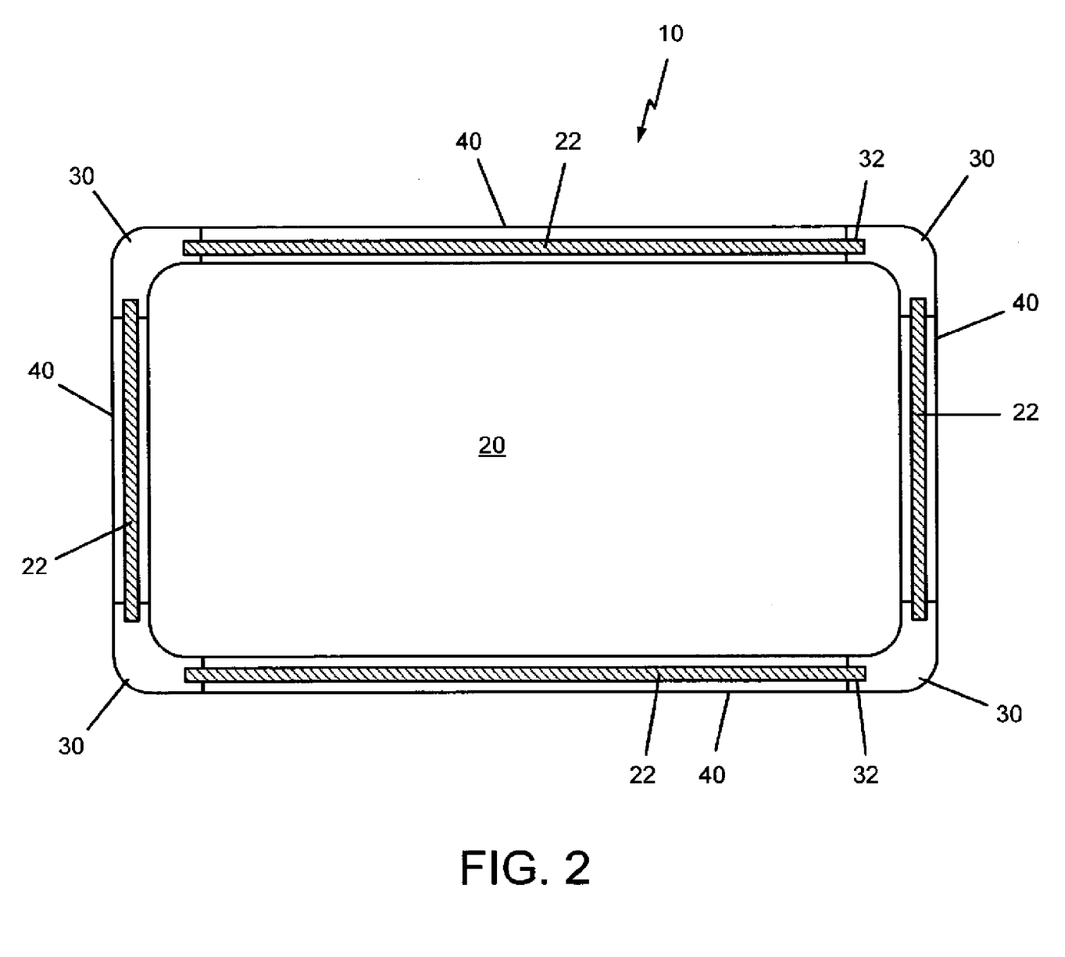
FIG. 2 is a cross-sectional view of the container of FIG. 1 along the line A-A, in accordance with the first exemplary embodiment of the present disclosure.

FIG. 2 is a cross-sectional view of the container 10 of FIG. 1 along the line A-A, in accordance with the first exemplary embodiment of the present disclosure. As can be seen in FIG. 2, the corner posts 30 have a uniform, consistent cross-section in a direction perpendicular to the line A-A (FIG. 1) and perpendicular to the plane of the paper. The sidewalls 22 also are shown with a consistently repeated cross-section in FIG. 2. FIG. 2 is representative of how the corner posts 30 may have the consistent cross-section such that all points along the length of the corner posts 30 are the same. This consistency in cross-section is applied to the bottom edge rails 40 and the top edge rail 50 (FIG. 1). Also shown in FIG. 2 are the slots 32 that may be formed within the corner posts 30. The slots 32 may be positioned along the length of the corner posts 30 such that their cross-sections remain uniform and consistent.

Figure 3:
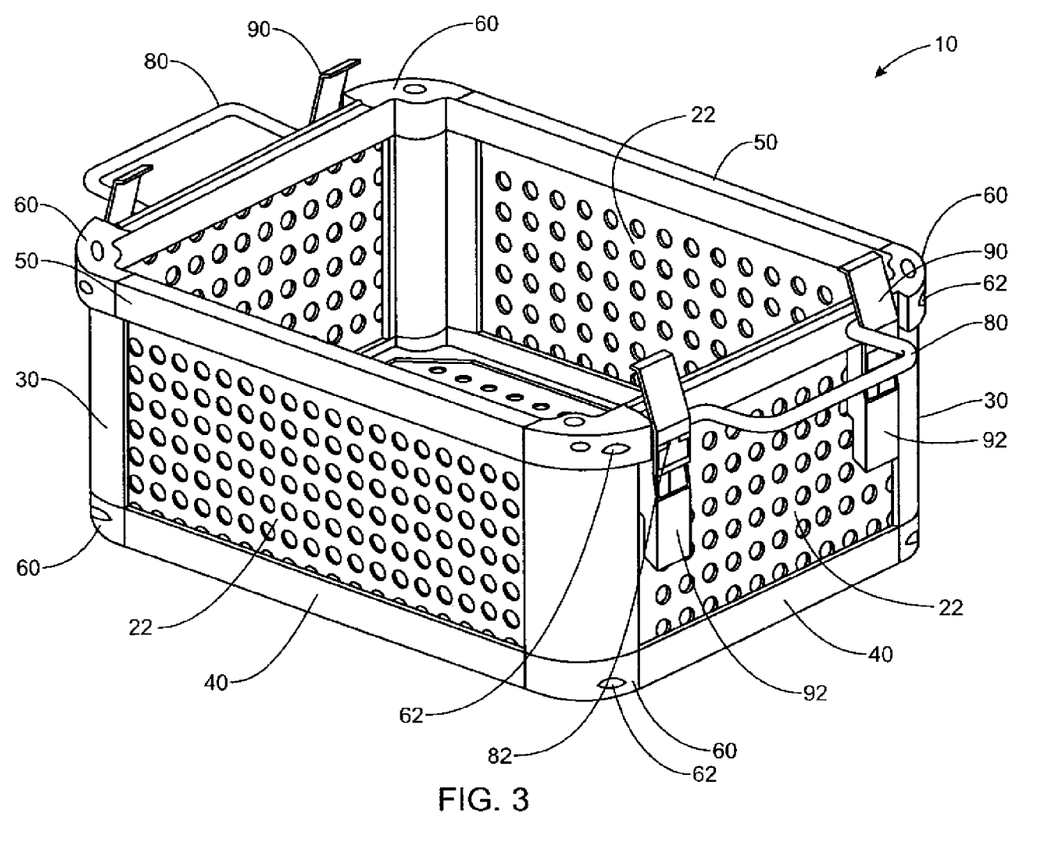
FIG. 3 is a plan view of the container of FIG. 1, in accordance with a first exemplary embodiment of the present disclosure.

FIG. 3 is a plan view of the container 10 of FIG. 1, in accordance with a first exemplary embodiment of the present disclosure. The container 10 may include one or more handles 80 that are affixed to a component of the container 10, such as the sidewall 22, the corner posts 30, or the bottom or top edge rails 40, 50. In FIG. 3, the handle 80 is affixed to the sidewall 22 with a bracket 82. The handle 80 may be rotatable to allow it to be stored proximate to the sidewall 22 when not in use. The container 10 may also include a retention device 90 that may be used to retain a cover 70 (FIG. 1) to the container 10, or retain one container 10 to another. The retention device 90 may utilize the same bracket 82 as the handle 80, or a different bracket. The retention device 90 may have an actuating arm 92 that allows for the retention device 90 to be moved between engaged and non-engaged positions. Any number of handles 80 and retention device 90 may be utilized with the container 10.

As is shown in FIG. 3, the fasteners 62 may be used to retain the junction connectors 30 to the bottom edge rails 40 and/or the top edge rails 50. The fasteners 62 may extend through a hole within the junction connectors 30 such that the ends of the fasteners may engage with the bottom or top edge rails 40, 50. Engagement may be achieved through threads on the fastener which connect to the end of the bottom or top edge rails 40, 50. The head of the fastener 62 may be housed within a recessed cavity or recess of the hole within the junction connector 62, such that the head does not interfere with the overall footprint of the container 10.

Figure 4:
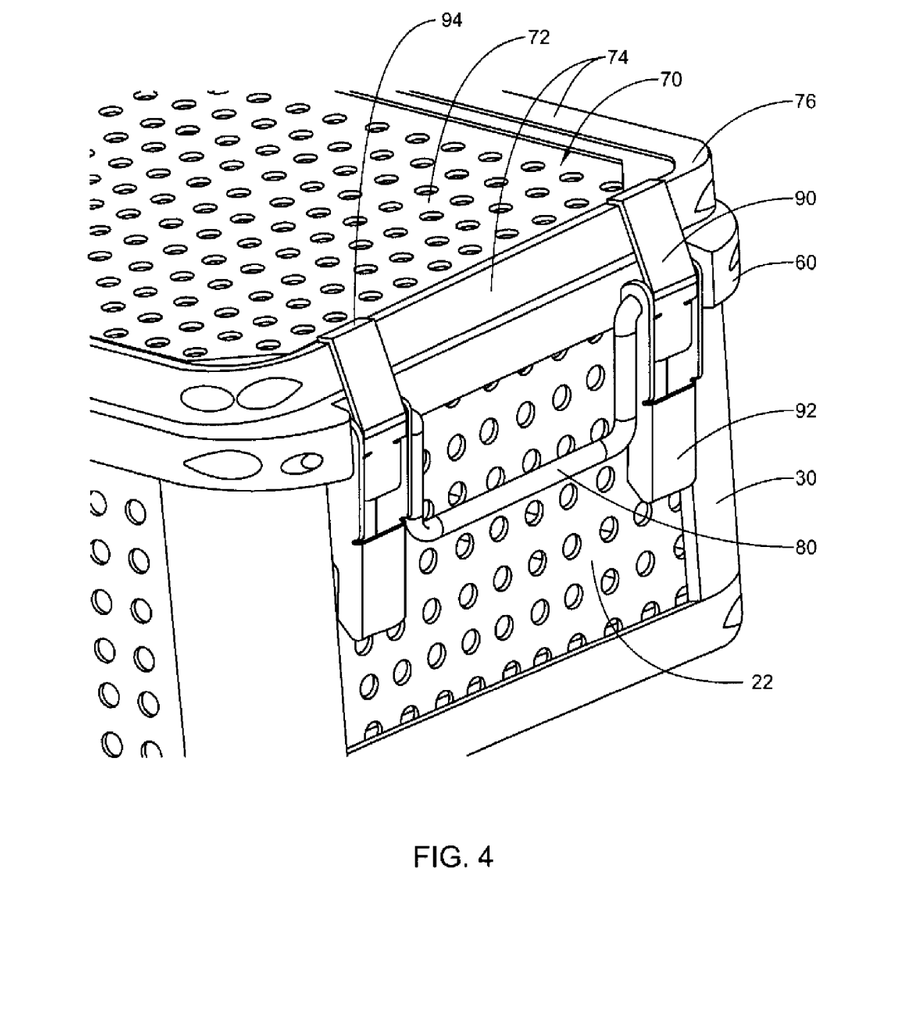
FIG. 4 is a plan view of the container of FIG. 1, in accordance with the first exemplary embodiment of the present disclosure.

FIG. 4 is a plan view of the container 10 of FIG. 1, in accordance with the first exemplary embodiment of the present disclosure. In particular, FIG. 4 depicts the container 10 with the retention devices 90 in an engaged position with a rail of the cover 70. The cover 70 may include the center portion 72, a plurality of edge rails 74, and a plurality of cover junction connectors 76 which connect together the plurality of edge rails 74 in the same fashion as described previously. The retention devices 90 are in the engaged position with edge rails 74 of the cover 70 when they are in a position retaining the cover 70 to the container 10. A hook end 94 of the actuating arms 92 may be positioned over a lip of the edge rails 74 of the cover 70. The actuating arms 92 are shown in the closed position, proximate to the sidewall 22. When the actuating arms 92 are rotated outwards from the bracket 82, the retention devices 90 may be moved to the non-engaged position, thereby removing the hook ends 94 of the actuating arms 92 from the edge rails 74 and allowing the cover 70 to be removed from the container 10.

Figure 5:
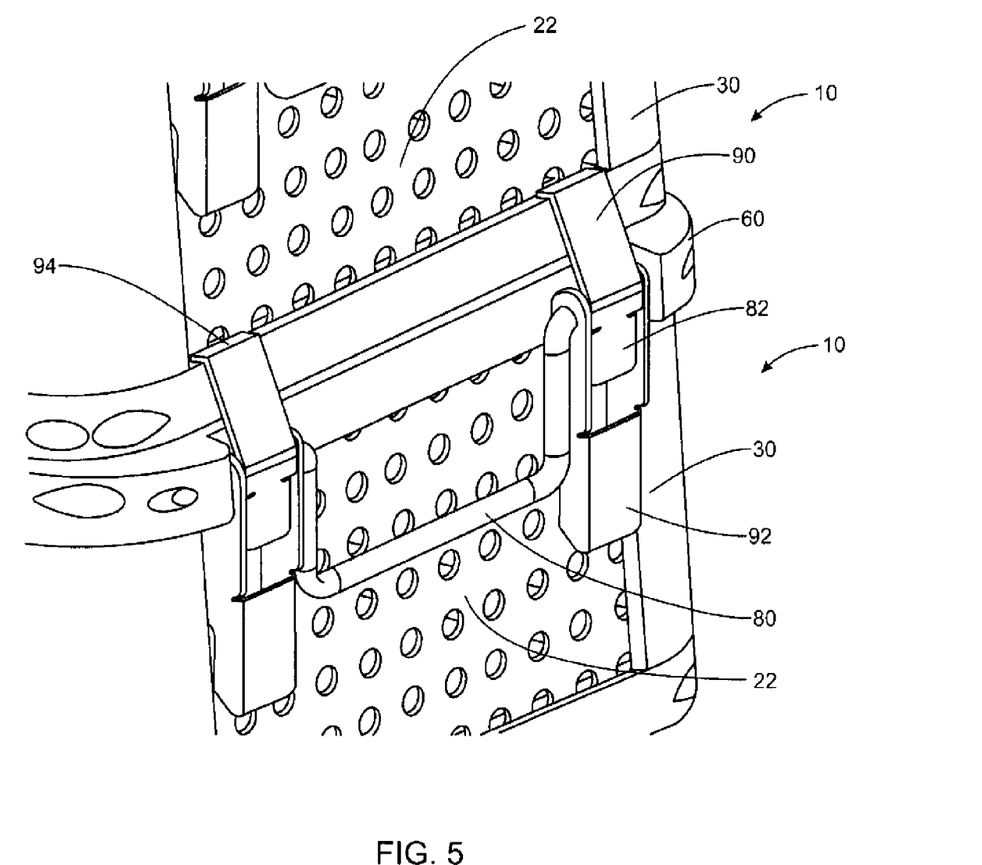
FIG. 5 is a plan view of the container of FIG. 1, in accordance with the first exemplary embodiment of the present disclosure.

FIG. 5 is a plan view of the container 10 of FIG. 1, in accordance with the first exemplary embodiment of the present disclosure. In particular, FIG. 5 depicts the container 10 with the retention devices 90 in an engaged position with a second container 10. As is shown, the hook ends 94 of the retention devices 90 may be used to retain the bottom of one container 10 to the top of another container 10. Similar to as described with respect to FIG. 4, the retention devices 90 are in the engaged position with the second container 10 when the hook ends 94 are capable of retaining the bottom edge rail 40 of the second container 10 to the top edge rail 50 of the first container 10. The actuating arms 92 are shown in the closed position, proximate to the sidewall 22. When the actuating arms 92 are rotated outwards from the bracket 82, the retention devices 90 may be moved to the non-engaged position, thereby allowing the second container 10 to be removed from the first container 10.

Figure 6:
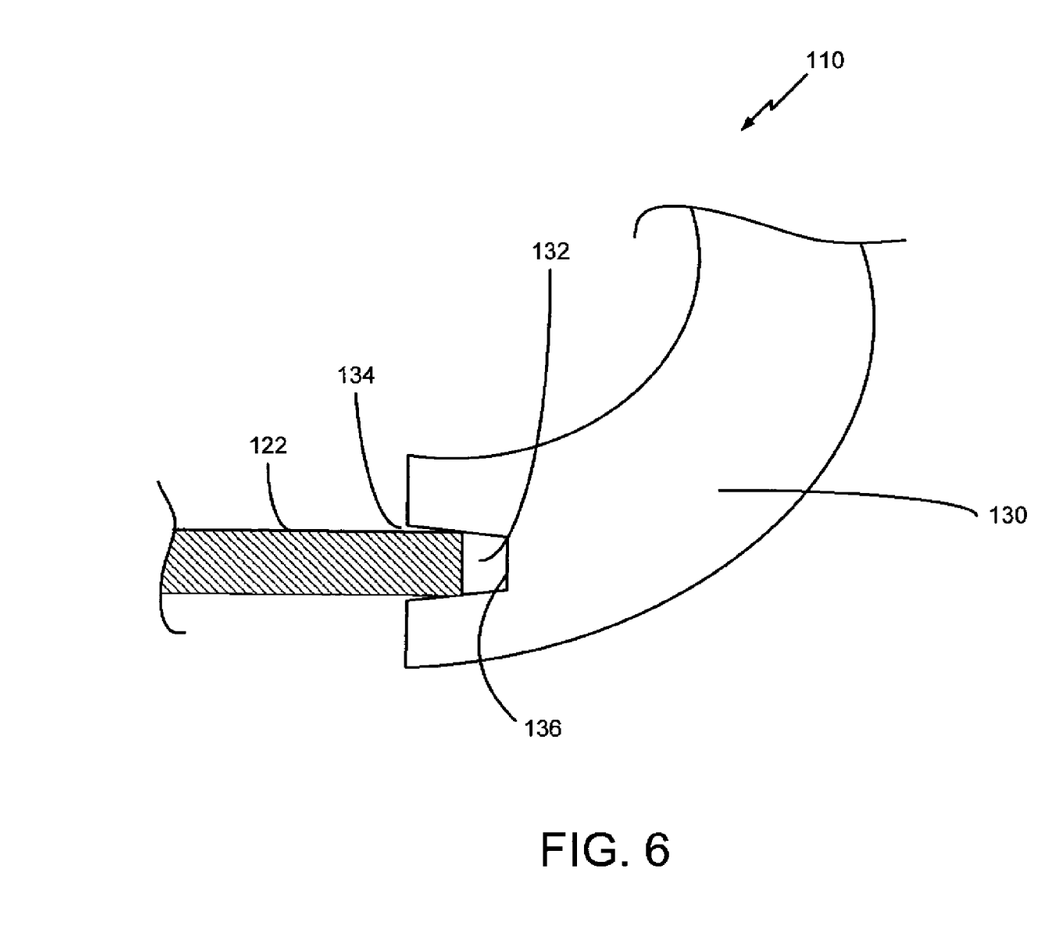
FIG. 6 is a partial cross-sectional view of the modular medical instrument sterilization container of FIG. 1 along the line A-A, in accordance with a second exemplary embodiment of the present disclosure.

FIG. 6 is a partial cross-sectional view of the modular medical instrument sterilization container 110 of FIG. 1 along the line A-A, in accordance with a second exemplary embodiment of the present disclosure. The modular medical instrument sterilization container 110, which may be referred to herein as "container 110" may include any of the components, features, and functions described within this disclosure. As is shown in FIG. 6, a partial cross-sectional view of the corner post 130 with slot 132 and sidewall 122 are shown. The slot 132, formed within the corner posts 130, may be positioned along the length of the corner posts 130 such that their cross-sections remain uniform and consistent. The slot 132 may be sized to receive the edges of the sidewalls 122. For example, the slot 132 may have a width that is slightly larger than a thickness of the sidewalls 122. The depth or other features of the slot 132 may vary depending on the design of the container 110 and its intended use. For example, the slot 132 may include an angled interior section, such that an outer portion 134 of the slot 132 is wider than an inner portion 136 of the slot 132, e.g., the portion of the slot 132 closes to a center of the corner post 130. An angled slot 132 within the corner post 130 may allow the edge of the sidewall 122 to fit snugly within the slot 132, as well as accommodate sidewalls 122 with varying thicknesses. For example, the angled slot 132 may be appropriate with a sidewall 122 having a thickness of ½ inch or a thickness of ⅝ inch.

Figure 7:
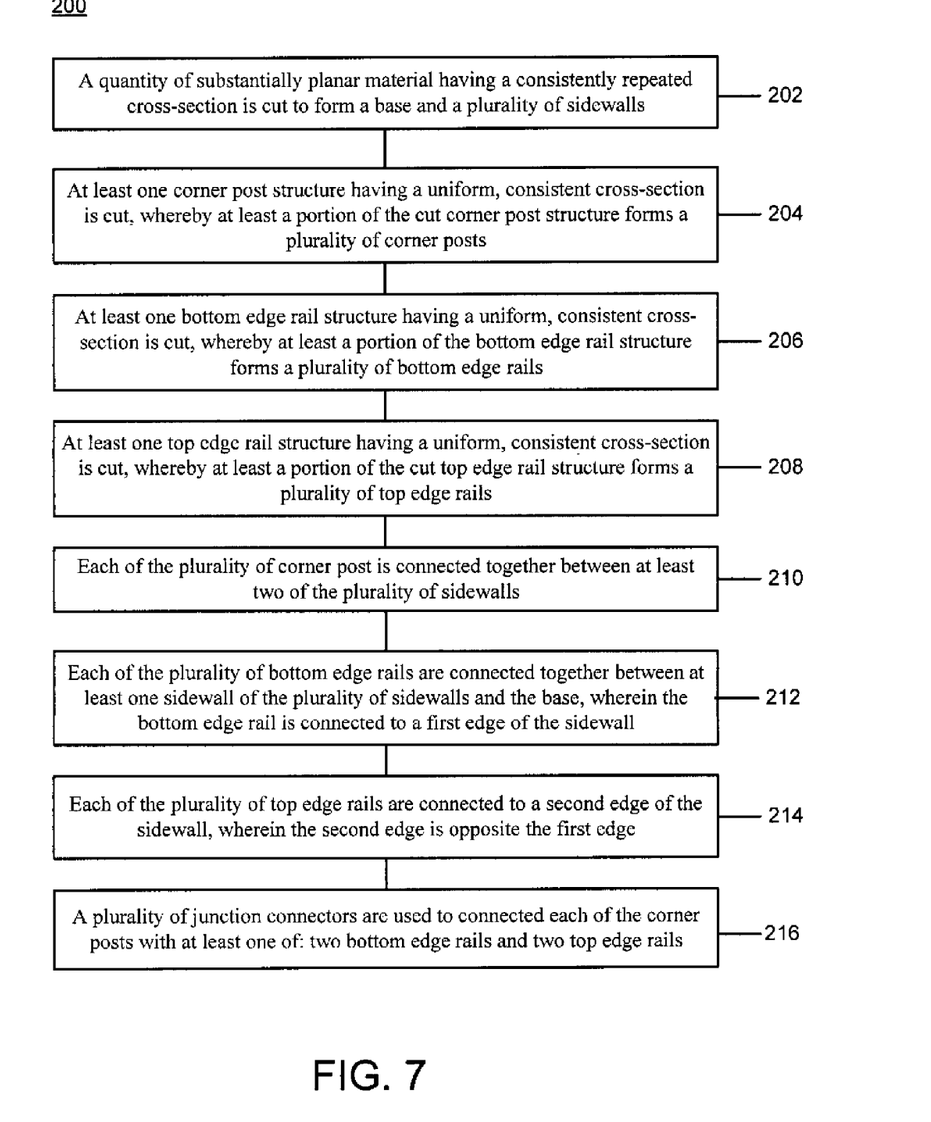
FIG. 7 is a flowchart illustrating a method for constructing a modular medical instrument sterilization container, in accordance with a third exemplary embodiment of the disclosure.

FIG. 7 is a flowchart 200 illustrating a method for constructing a modular medical instrument sterilization container in accordance with a third exemplary embodiment of the disclosure. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 202, a quantity of substantially planar material having a consistently repeated cross-section is cut to form a base and a plurality of sidewalls. At least one corner post structure having a uniform, consistent cross-section is cut, whereby at least a portion of the cut corner post structure forms a plurality of corner posts (block 204). At least one bottom edge rail structure having a uniform, consistent cross-section is cut, whereby at least a portion of the bottom edge rail structure forms a plurality of bottom edge rails (block 206). At least one top edge rail structure having a uniform, consistent cross-section is cut, whereby at least a portion of the cut top edge rail structure forms a plurality of top edge rails (block 208). Each of the plurality of corner post is connected together between at least two of the plurality of sidewalls (block 210). Each of the plurality of bottom edge rails are connected together between at least one sidewall of the plurality of sidewalls and the base, wherein the bottom edge rail is connected to a first edge of the sidewall (block 212). Each of the plurality of top edge rails are connected to a second edge of the sidewall, wherein the second edge is opposite the first edge (block 214). A plurality of junction connectors are used to connected each of the corner posts with at least one of: two bottom edge rails and two top edge rails (block 216).

The method may include any additional number of steps, processes, functions, or variations thereof, including any of the functions described relative to FIGS. 1-6. For example, connecting together each of the plurality of corner post between the at least two of the plurality of sidewalls may include inserting a third edge of each of the at least two plurality of sidewalls into a slot formed within each of the plurality of corner posts, wherein the slot is positioned along a length of each of the plurality of corner posts. Similarly, each of the plurality of bottom and top edge rails may have a slot positioned along their length which the sidewall is inserted within. Fasteners may be used to secure the structures together, including a fastener that is at least partially positioned within a hole within each of the plurality of junction corners, wherein an end of the at least one fastener extends beyond within the hole to connect to at least one of the two bottom edge rails and the two top edge rails.

In manufacturing the sterilization container, the various structures, including the corner post structure, the bottom edge rail, and the top edge rail structure may be cut according to a desired length. While further processing of the cut end of these structures may be available, processing may be limited. For example, the cut ends may be sanded to remove rough edges or cut residue, but may be otherwise left untouched and not further processed. Other processing techniques, known in the art but not specifically discussed herein, may also be used.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

What is claimed is:

1. A modular medical instrument sterilization container comprising:

a base and a plurality of sidewalls, wherein the base and the plurality of sidewalls are both substantially planar and have a consistently repeated cross-section;

a plurality of corner posts, wherein at least one of the plurality of corner posts is connected between at least two of the plurality of sidewalls, wherein all of the plurality of corner posts have a uniform, consistent cross-section along a length;

a plurality of bottom edge rails, wherein at least one of the plurality of bottom edge rails is connected between at least one of the plurality of sidewalls and the base, wherein the bottom edge rail is connected to a first edge of the at least one sidewall, wherein all of the plurality of bottom edge rails have a uniform, consistent cross-section along a length;

a plurality of top edge rails, wherein at least one of the plurality of top edge rails is connected to a second edge of the at least one sidewall, wherein the second edge is opposite the first edge, wherein all of the plurality of top edge rails have a uniform, consistent cross-section along a length; and a plurality of junction connectors, each of the plurality of junction connectors connected to one of the plurality of corner posts and to at least one of:

two of the plurality of bottom edge rails; and two of the plurality of top edge rails, wherein each of the plurality of junction corners further comprise at least one fastener positioned at least partially within a hole within each of the plurality of junction corners, wherein an end of the at least one fastener extends beyond the hole.

2. The modular medical instrument sterilization container of claim 1, wherein the hole has a recessed cavity, wherein a head of the at least one fastener is positioned within the recessed cavity.

* * * * *